United States Patent [19]

Matassa

[11] Patent Number: 5,041,460

[45] Date of Patent: Aug. 20, 1991

[54] HETERA-ALIPHATIC CARBOXAMIDES

[75] Inventor: Victor G. Matassa, Chadds Ford, Pa.

[73] Assignee: ICI Americas Inc., Wilmington, Del.

[21] Appl. No.: 336,972

[22] Filed: Apr. 12, 1989

Related U.S. Application Data

[63] Continuation-in-part of Ser. No. 181,334, Apr. 14, 1988, abandoned.

[51] Int. Cl.$^5$ .................... C07D 209/20; A61K 31/40
[52] U.S. Cl. ............................... 514/415; 514/339; 514/414; 514/418; 546/273; 548/510; 548/511
[58] Field of Search ............... 548/511, 510; 514/414, 514/415, 418, 339; 546/273

[56] References Cited

FOREIGN PATENT DOCUMENTS

179619A1 4/1986 European Pat. Off. .
0220066 4/1987 European Pat. Off. .
0227241 7/1987 European Pat. Off. .

OTHER PUBLICATIONS

J. L. Marx, Science (1982) 215, 1380: "The Leukotrienes in Allergy and Inflammation".

J. A. Cook, et al., J Pharm. Exp. Ther. (1985) 235, 470: "Protective Effect of a Selective Leukotriene Antagonist in Endotoxemia in the Rat".

C. Denzlinger, et al., Science (1985) 230, 330: "Leukotrienes as Mediators in Tissue Trauma".

R. D. Krell, J. Pharm. Exp. Ther. (1979) 211, 436: "Pharmacologic Characterization of Isolated Rhesus Monkey Brochial Smooth Muscle".

D. Aharony, et al., Fed Proc. (1987) 46, 691: "Inhibition of $^3$H-Leukotriene (LT) $D_4$ Binding to Guinea-pig Lung Membrane Receptors by the Novel Leukotriene Antagonist ICI 198,615".

Yung-chi Cheng and W. H. Prusoff, Biochem. Pharmacol. (1973) 22, 3099–3108: "Relationship Between the Inhibition Constant ($K_l$) and the Concentration of Inhibitor Which Causes 50 Per Cent Inhibition ($I_{50}$) of an Enzymatic Causes 50 Reaction".

Primary Examiner—Robert A. Wax
Assistant Examiner—Frederick F. Tsung
Attorney, Agent, or Firm—Rosemary M. Miano; Thomas E. Jackson

[57] ABSTRACT

This invention provides a series of novel heter-aliphatic carboxamides of formula I in which the group >Z—Y—X< is selected from >C=CH—N<, >N—CH=C<, >C=N—N< and >N—N=C< and the other radicals have the meanings defined in the following specification. The compounds of formula I are leukotriene antagonists. The invention also provides pharmaceutically acceptable salts of the formula I compounds; pharmaceutical compositions containing the formula I compound, or their salts, for use in the treatment of, for example, allergic or inflammatory diseases, or endotoxic or traumatic shock conditions; and processes for the manufacture of the formula I compounds, as well as intermediates for use in such manufacture.

10 Claims, No Drawings

HETERA-ALIPHATIC CARBOXAMIDES

This application is a continuation-in-part of Ser. No. 181,334, April 14, 1988, abandoned.

BACKGROUND AND SUMMARY OF THE INVENTION

This invention concerns novel hetera-aliphatic carboxamide derivatives, and, particularly, certain urethanes and ureas, which antagonize the actions of one or more of the arachidonic acid metabolites known as leukotrienes (hereinafter referred to as "leukotriene antagonist properties"). The novel derivative are useful whenever such antagonism is desired. Thus, such compounds may be of value in the treatment of those diseases in which leukotrienes are implicated, for example in the treatment of allergic disorders, such as, for example, asthma, or of inflammatory diseases, or of endotoxic or traumatic shock conditions. The invention also provides pharmaceutical compositions treatments, and processes and intermediates for the manufacture of the novel derivatives.

In European Patent Application publication number 0 179 619 A1 are disclosed N-acylated derivatives of a series of indoles, indazoles and indolines having an amino group in the benzenoid ring and which possess leukotriene antagonizing properties. I have now disclosed a series of indoles and indazoles which have a hetera-aliphatic carboxamidic substituent in the benzenoid ring and which unexpectedly posses the property of antagonizing one or more of the arachidonic acid metabolites known as leukotrienes, and this is the basis for my invention.

DESCRIPTION OF THE INVENTION

According to the invention there is provided a compound of formula I (formula set out, together with other formulae referred to by Roman numerals, on pages following the Examples) wherein:

the group >Z—Y—X< is selected from a group consisting of:
(a) >C=CR$^a$—N<,
(b) >N—CR$^a$=C<,
(c) >C=N—N< and
(d) >N—N=C<;

in which ">" indicates two separate bonds;

the radicals R$^a$, if present, and R$^b$ are together selected from a group consisting of
(i) R$^a$, if present, and R$^b$ are each hydrogen,
(ii) R$^a$ is chloro and R$^b$ is hydrogen,
(iii) R$^a$ is bromo and R$^b$ is hydrogen and
(iv) R$^a$, if present, and R$^b$ are each chloro;

the radicals R$^1$ and R$^2$ are selected from a group consisting of
(i) R$^1$ and R$^2$ are each independently selected from a group consisting of hydrogen, (1–6C)alkyl optionally containing a double or triple bond, (3–6C)cycloalkyl and (3–6C)cycloalkyl(1–4C)alkyl wherein a cycloalkyl group or the cycloalkyl portion of a cycloalkyl group may optionally contain a double bond and may optionally bear 1 or 2 (1–3C)alkyl groups, and
(ii) R$^1$ and R$^2$, together with the nitrogen to which they are attached, form a pyrrolidino, piperidino, piperazino, morpholino or thiomorpholino ring, which ring may optionally bear one to three methyl groups;

R$^9$ is selected from a group consisting of hydrogen, (1–6C)alkyl optionally containing a double or triple bond, (3–6C)cycloalkyl and (3–6C)cycloalkyl(1–4C)alkyl wherein a cycloalkyl group or the cycloalkyl portion of a cycloalkylalkyl group may optionally contain a double bond and may optionally bear 1 or 2 (1–3C)alkyl groups;

Q is oxygen or an imino group of formula —NR$^3$—, wherein R$^3$ is hydrogen or methyl;

M is a (1–5C)alkylene group wherein the chain joining Q with the benzenoid ring contains from 1 to 3 carbons;

R$^{11}$ is selected from hydrogen, (1–4C)alkoxy, (1–2C)alkyl and hydroxy;

R$^{12}$ is selected from a group consisting of (6–12C)aryl, heteroaryl, and (6–12C)aryl(1–4C)alkyl, in any of which the aromatic or heteroaromatic moiety may optionally bear 1 or 2 substituents selected from a group consisting of halogeno, (1–4C)alkyl, (1–4C)alkoxy, trifluoromethyl and amino;

and salts thereof, especially pharmaceutically acceptable salts.

It will be appreciated that certain of the compounds of formula I may contain an asymmetrically substituted carbon atom, may exist in, and be isolated in, optically-active and racemic forms. In addition, it will be appreciated that certain compounds of formula I, for example, those containing a double bond, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine the leukotriene antagonist properties by the standard tests described hereinafter.

In this specification R$^1$, R$^2$, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Heteroaryl means a monocyclic or fused bicyclic ring system of from 5 to 11 atoms containing at least one 5- or 6-membered aromatic ring and consisting of from 1 to 10 carbons and from 1 to 4 heteroatoms each of which is selected independently from a group consisting of oxygen, sulfur, and nitrogen. Halogeno is fluoro, chloro, bromo or iodo.

Particular values for R$^1$, R$^2$ or R$^9$ when it is (1–6C)alkyl include, for example, methyl, ethyl, propyl, isopropyl, butyl, 1-methylpropyl, 2-methylpropyl, pentyl, 1-ethylpropyl, 3-methylbutyl, hexyl, and 4-methylpentyl; and when the alkyl group contains an optional double or triple bond, particular values include allyl, 2-methylprop-2-enyl, 3-methylbut-3-enyl and 2-propynyl.

Particular values for R$^1$, R$^2$ or R$^9$ when it is (3–6C)cycloalkyl include, for example, cyclopropyl, cyclobutyl, cyclopentyl, and cyclohexyl; and when the cycloalkyl group contains an optional double bond or alkyl substituent, particular values include cyclopentenyl, cyclohexenyl and methylcyclobutyl.

Particular values for $R^1$, $R^2$ or $R^9$ when it is (3–6C)cycloalkyl(1–4C)alkyl include, for example, cyclopropylmethyl, cyclobutylmethyl, cyclopentylmethyl, cyclohexylmethyl, 1-cyclopentylethyl and 2-cyclopentylethyl; and when the cycloalkyl portion contains an optional double bond or alkyl substituent, particular values include methylcyclopentylethyl.

Particular values for the group $R^1R^2N$ when $R^1$ and $R^2$, together with the nitrogen to which they are attached, form a ring include, for example, pyrrolidino, piperidino, 4-methylpiperazino and morpholino.

Particular values for M include, for example, methylene, ethan-1,2-diyl, propan-1,3-diyl, propan-1,2-diyl, 2-methylpropan-1,2-diyl and butan-1,3-diyl.

Particular values for $R^{11}$ when it is (1–4C)alkoxy include, for example, methoxy, ethoxy and propoxy; and when it is (1–2C)alkyl, particular values include methyl and ethyl.

Particular values for $R^{12}$ when it is (6–12C)aryl include, for example, phenyl and naphthyl; when $R^{12}$ is heteroaryl, thienyl, furyl and pyridyl; and when $R^{12}$ is (6–12C)aryl(1–4C)alkyl, phenylmethyl, 2-phenylethyl and 3-phenylpropyl. Particular values for an optional substituent on the aromatic or heteroaromatic portion of $R^{12}$ include, for example, fluoro, chloro, bromo, methyl, ethyl, methoxy, ethoxy, trifluoromethyl and amino.

More particular values for the radicals for a compound of formula I are independently selected from those listed below.

More particular values and ranges for the values of $R^1$, $R^2$ and $R^9$ are each independently selected from a group consisting of hydrogen, (1–4C)alkyl optionally containing a double bond, (3–5C)cycloalkyl and (3–5C)cycloalkyl(1–2C)alkyl.

More particular values for the group $R^1R^2N$ when $R^1$ and $R^2$, together with the nitrogen to which they are attached, form a ring include pyrrolidino and morpholino.

More particular values and a range for the values of M include a (1–3C)alkylene group.

More particular values and ranges for the values of $R^{11}$ include hydrogen and (1–2C)alkoxy.

More particular values for $R^{12}$ include phenyl (optionally substituted by methyl, chloro, bromo, fluoro or methoxy), pyridyl, and thienyl.

Typical values for the radicals and groups for a compound of formula I are independently selected from those listed below.

A typical value for $R^1$ or $R^2$ when it is (1–4C)alkyl is methyl.

A typical value for the group $R^1R^2N$ when $R^1$ and $R^2$, together with the nitrogen to which they are attached, form a ring is morpholino.

A typical value for $R^9$ when it is (1–6C)alkyl is methyl or propyl.

A typical value of Q is imino of formula —$NR^3$—.

A typical value of $R^3$ is hydrogen.

A typical value of M is ethylene.

A typical value for each of $R^a$ and $R^b$ is hydrogen.

A typical value for $R^{11}$ is methoxy.

A typical value for is $R^{12}$ is 2-chlorophenyl or 2-methylphenyl.

It is preferred that when $R^{12}$ is a substituted phenyl that the substituent be in the "2" position.

It will be appreciated that within the above definitions there are included a number of sub-groups of compounds, for example (a) indoles of formula Ia,
(b) inverted indoles of formula Ib,
(c) indazoles of formula Ic, and
(d) inverted indazoles of formula Id, wherein $R^a$, $R^b$, $R^1$, $R^2$, $R^9$, Q, M, $R^{11}$, and $R^{12}$ have any of the values defined above for a compound of formula I, together with the pharmaceutically acceptable salts thereof.

A preferred subgroup is that of compounds of formula Ib. Preferred values for radicals and groups of a compounds of formula Ib include, for example, those listed above as typical values for a compound of formula I.

Preferred compounds of the invention include 4-[5-[2-(N',N'-dimethylureido)ethyl]-1-propylindol-3-ylmethyl]-3-methoxy-N-(2-methylphenylsulfonyl)benzamide; 4-[5-[2-(N',N'-dimethylureido)ethyl]-1-methylindol-3-ylmethyl]-3-methoxy-N-(2-methylphenylsulfonyl)benzamide; and 4-[5-[2-(N',N'-dimethylureido)ethyl]-1-methylindol-3-ylmethyl]-3-methoxy-N-(2-chlorophenylsulfonyl)benzamide; and the pharmaceutically acceptable salts thereof.

Examples of suitable pharmaceutically acceptable salts are salts formed with bases which form a physiologically acceptable cation, such as alkali metal (especially sodium or potassium), alkaline earth metal (especially calcium or magnesium), aluminum or ammonium salts, as well as salts made with appropriate organic bases such as triethylamine, morpholine, piperidine or triethanolamine. For those compounds of formula I which are sufficiently basic, examples of suitable pharmaceutically acceptable salts include acid-addition salts such as those made with a strong acid, for example hydrochloric, sulfuric or phosphoric acid.

The compounds of formula I may be made by processes which include processes known in the chemical art for the production of structurally analogous heterocyclic compounds. Such processes for the manufacture of a compound of formula I as defined above are provided as further features of the invention and are illustrated by the following procedures in which the meanings of generic radicals are as defined above:

(A) Reacting a compound of formula III wherein $R^{10}$ is carboxy (which compound is hereinafter referred to as "acid of formula III") with a sulfonamide derivative of formula $R^{12}.SO_2.NH_2$ in the presence of a dehydrating agent or reacting a reactive derivative of an acid of formula III with a sulfonamide, or a salt thereof, of formula $R^{12}.SO_2.NH_2$.

Thus, for example, a free acid of formula III may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with a sulfonamide of formula $R^{12}.SO_2.NH_2$ in the presence of a suitable solvent or diluent, for example, methylene chloride at a temperature in the range of, for example, 10° to 50° C., but preferably at or near ambient temperature.

Alternatively, a reactive derivative of an acid of formula III, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt)

of the appropriate sulfonamide of formula $R^{12}.SO_2.NH_2$, conveniently at or near ambient temperature and in a suitable solvent or diluent, for example, tetrahydrofuran, dimethylformamide or methylene chloride.

An acid of formula III wherein $R^{10}$ is a carboxy group may be obtained by decomposing a suitable ester of formula III in which $R^{10}$ is $COOR^h$ wherein $R^h$ is a conveniently removed acid protecting group (which compound is hereinafter referred to as "ester of formula III"), for example, phenyl, benzyl, or (1-6C)alkyl optionally bearing an acetoxy, (1-4C)alkoxy or (1-4C)alkylthio substituent. A particular value for $R^h$ is, for example, methyl, ethyl, propyl, t-butyl, acetoxymethyl, methoxymethyl, 2-methoxyethyl, methylthiomethyl, phenyl, or benzyl.

The starting acids of formula III wherein $R^{10}$ is carboxy are active as leukotriene antagonists, and they are included within the scope of the invention. In addition, certain of the corresponding esters of formula III wherein $R^{10}$ is $COOR^h$ may be active in their own right as leukotriene antagonists (such as, for example, by in vivo conversion to the corresponding carboxylic acid), for example, those wherein $R^h$ is (1-6C)alkyl, and they are also included within the scope of the invention.

It will be appreciated that the decomposition of an ester of formula III can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when $R^h$ is methyl, the ester may be decomposed by nucleophilic demethylation with, for example, lithium thioethoxide in a solvent such as N,N'-dimethylpropyleneurea. Alternatively, it may in certain circumstances, for example, when $R^h$ is t-butyl, be possible to carry out the decomposition by thermal means, for example, by heating the ester of formula III at a temperature of, for example, 100°-150° C., alone or in a suitable solvent or diluent such as diphenylether. In addition, when $R^h$ is t-butyl, the decomposition may be performed, for example, by using trimethylsilyl triflate and then water, in a conventional manner. Still further, in certain circumstances, for example, when $R^h$ is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15°-100° C. and conveniently at or near ambient temperature. When such a method is employed, the resulting carboxylic acid of formula III, wherein $R^{10}$ is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulfuric acid.

(B) Acylating an alcohol or an amine of formula IV wherein A has the value —QH with an acid halide of formula $R^1R^2NCOCl$ or (when $R^2$ is hydrogen) with an isocyanate of formula $R^1NCO$.

When an acid halide is used as the acylating agent, a suitable base such as triethylamine, 4-methylmorpholine, pyridine, 2,6-lutidine or 4-dimethylaminopyridine is conveniently also employed, preferably together with a suitable inert solvent or diluent, for example, dichloromethane, diethyl ether, tetrahydrofuran or 1,2-dimethoxyethane. In general, the acylations are carried out at a temperature in the range of, for example, −20° to 60° C. and, conveniently, at or near ambient temperature.

(C) Reduction of the double bond of a compound of formula I in which $R^1$, $R^2$ or $R^9$ contains one double bond to provide a corresponding compound of formula I in which $R^1$, $R^2$ or $R^9$ contains no double bond, or reduction of a double bond of a compound corresponding to a compound of formula I, but in which the link corresponding to M contains a double bond, to afford a corresponding compound of formula I.

Preferred reduction conditions include, for example, catalytic hydrogenation over palladium on carbon in a suitable solvent such as methanol, ethanol, ethyl acetate, or tetrahydrofuran at ambient temperature, and, optionally, the addition of an equivalent of a base, such as, for example, potassium hydroxide or triethylamine.

(D) For a compound of formula I wherein >Z—Y—X—< has the value (b) or (d) and $R^9$ is not hydrogen, reacting a corresponding imine of formula I wherein >Z—Y—X—< has the value (b) or (d) and $R^9$ is hydrogen with a reagent of formula $R^9.U$, wherein U is a suitable leaving group, for example, chloro, bromo, iodo, methanesulfonyloxy or p-toluenesulfonyloxy.

The reaction is preferably performed in the presence of a suitable base, for example, an alkali metal hydride such as sodium or potassium hydride in a suitable inert solvent or diluent, for example, tetrahydrofuran, 1,2-dimethoxyethane, N-methylpyrrolidone, or N,N-dimethylformamide. Alternatively, the compound of formula I may be used in the form of its preformed anhydrous alkali dimetal salt, for example, by prior reaction with a suitable base such as sodium or potassium methoxide, t-butoxide or hydride, or butyl lithium, in which case a wider range of conventional solvents or diluents may be employed for the reaction with the alkylating agent. In either case, the alkylation is generally performed at a temperature in the range of, for example, −10° to 40° C. and, conveniently, at or near ambient temperature.

(E) For a compound of formula I wherein Q has the value —$NR^3$— and $R^3$ is hydrogen, reacting an amine of formula $R^1R^2NH$ with a corresponding isocyanate of formula IV wherein A has the value —NCO.

The reaction may be carried out by in situ formation of the isocyanate of formula IV wherein A has the value —NCO from a corresponding acid of formula IV wherein A has the value —COOH using a similar method to that described in Example 2, part a, for the preparation of a compound of formula III.

It may be desired to optionally use a protecting group during all or portions of the above described processes (A)-(E); the protecting group then may be removed when the final compound is to be formed.

Pharmaceutically acceptable salts may be obtained using standard procedures well known in the art, for example, by reacting a compound of formula I with a suitable base affording a physiologically acceptable cation or by reacting a sufficiently basic compound of formula I with a suitable acid affording a physiologically acceptable anion.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures or the procedures described in the examples.

In general, the preparation of the starting materials of formulae III and IV may begin with an appropriate heterocycle having a simple substituent at the position of attachment of the group $R^1R^2N.CO.Q.M-$, for example, 5-cyanoindole. By introduction of the required substituents at X and Z on the heterocyclic ring, followed by elaboration of the side chain joined to the benzenoid ring at the M-position and introduction of substituents at $R^a$ and $R^b$ when $R^a$ or $R^b$ is not hydrogen, the desired starting materials may be obtained. It will be clear to one skilled in the art that the order of steps for the introduction onto the heterocyclic ring of the various groups at $R^a$, $R^b$, X and Z and the elaboration of the side chain $R^1R^2N.CO.M-$ may be varied according to considerations of convenience, protecting groups, presence of reactive groups, etc. The introduction of each group will therefore be described independently.

Routes for the introduction of substituents at positions X and Z of the heterocyclic rings (in which $R^a$, if present, and $R^b$ are each hydrogen) are illustrated in Schemes Ia-Id. In these schemes, $R^c$ may represent the group $R^1R^2N.CO.Q.M-$ or, more preferably, an intermediate or precursor to that group, such as, for example, cyano, formyl, or carbomethoxy, as described hereinbelow; U may represent a leaving group, especially bromo; and V may represent a halogeno group.

Intermediates which are indoles may be prepared by using sequences illustrated in Scheme Ia. Thus, an indole of formula 20 may be formylated to provide a 3-formylindole of formula 21, which may be further converted into a benzylated derivative of formula 22 by alkylation with a substituted benzyl compound of formula 23. By further elaboration of the 3-formyl group into a group of formula $R^9$ using conventional methods, a compound of formula 22 may be converted into a corresponding compound of formula Va. Alternatively, an indole of formula 20 may be alkylated at the 3-position using, for example, silver carbonate, and a sufficiently reactive alkylating agent of formula $R^9.V$, especially wherein V is bromo or chloro, to afford an indole of formula 25. An indole of formula 25 may be alkylated with a compound of formula 23 to provide an intermediate of formula Va.

Intermediates which are "inverted indoles" may be prepared by using a sequence illustrated in Scheme Ib. Thus, an indole of formula 26 may be alkylated using, for example, silver carbonate, and a compound of formula 23 to afford an indole of formula 27. By introduction of the $R^9$ group using a conventional procedure, including a similar procedure to process (D), an indole of formula 27 may be converted into a corresponding indole of formula Vb.

Intermediates which are indazoles may be prepared using a sequence illustrated in Scheme Ic. Thus, an indazole of formula 29 may be halogenated to afford an indazole of formula 30, especially one wherein V is chloro or bromo. An indazole of formula 30, conveniently as the sodium salt, may be treated with an alkylating agent of formula 23 to afford an indazole of formula 31. To obtain an indazole of formula Vc wherein $R^9$ is hydrogen, the V-group of an indazole of formula 31 may be removed reductively. To introduce other values of $R^9$, an indazole of formula 31 may be substituted at the 3-position by a transition metal catalyzed cross coupling reaction, followed by elaboration of the group introduced as necessary to provide $R^9$ using conventional methodology.

Intermediates which are "inverted indazoles" may be prepared by using a sequence illustrated in Scheme Id. Thus, an indazole of formula 33 may be halogenated to afford an indazole formula 34, especially one wherein V is bromo. An indazole of formula 34, conveniently as the sodium salt, may be alkylated with a reagent of formula $U.R^9$ to afford a corresponding indazole of formula 35. By using a cross coupling reaction using a transition metal catalyst such as, for example, dichloro[1,1'-bis(diphenylphosphino)ferrocene]palladium(II), and a compound of formula 23 wherein U is, for example, bromo, an indazole of formula 34 may be converted into an indazole of formula Vd.

An intermediate of formula V wherein $R^a$, if present, and $R^b$ are each hydrogen, (i.e., a selected intermediate of formula Va, Vb, Vc or Vd) may be converted into a corresponding starting material of formula III or formula IV by a conventional method, such as, for example, described in the examples and described below. A compound of formula V in which $R^c$ is cyano may be reduced to a corresponding compound of formula V in which $R^c$ is formyl using, for example, a similar method to the one described in Example 1, part b, to serve as a general intermediate for the introduction of the side chain of formula $R^1R^2N.CO.Q.M-$. Examples of routes to corresponding compounds of formula III, wherein $R^{10}$ is $COOR^h$ are outlined in Scheme II. Intermediates of formula III, wherein $R^a$, if present, and $R^b$ are hydrogen and is $COOR^h$ conveniently may be converted into corresponding intermediates of formula III wherein $R^{10}$ is $COOR^h$ and wherein $R^a$ is chloro and $R^b$ is hydrogen; wherein $R^a$ is bromo and $R^b$ is hydrogen and wherein $R^a$, if present, and $R^b$ are each chloro. Thus an ester of formula III wherein $R^{10}$ is $COOR^h$ and wherein $R^a$ is present and $R^a$ and $R^b$ are each hydrogen may be treated with one molar equivalent of N-chlorosuccinimide or N-bromosuccinimide, respectively, in an inert solvent, for example in a manner similar to that described in Example 10, part a, to afford a corresponding ester of formula III wherein $R^{10}$ is $COOR^h$ wherein $R^a$ is chloro and $R^b$ is hydrogen or wherein $R^a$ is bromo and $R^b$ is hydrogen, respectively. Similarly, an ester of formula III wherein $>Z—Y—X<$ is $>N—CR^a=C<$ and $R^{10}$ is $COOR^h$ and wherein $R^a$ and $R^b$ are both hydrogen may be treated with at least two molar equivalents of N-chlorosuccinimide in an inert solvent, for example in a manner similar to that described in Example 12, part a, to provide a corresponding ester of formula III wherein $R^{10}$ is $COOR^h$ and wherein $R^a$ and $R^b$ are both chloro.

If an intermediate of formula IV wherein A is QH is desired, it may be obtained from a corresponding compound of formula V wherein $R^c$ has the value $HQ.M—$ by a sequence of (i) protecting the HQ-group with a conventional hydroxy or amino-protecting group, (ii) decomposing the ester of formula —COOR$^h$ to afford the corresponding acid, (iii) coupling the acid with a sulfonamide of formula R$^{12}$.SO$_2$.NH using a similar process to method (A), and (iv) deprotecting the HQ-group to provide a compound of formula IV.

As stated previously, the compounds of formula I possess leukotriene antagonist properties. Thus, they antagonize at least one of the actions of one or more of the arachidonic acid metabolites known as leukotrienes, for example, C4, D4, and/or E4, which are known to be powerful spasmogens (particularly in the lung), to increase vascular permeability and which have been implicated in the pathogenesis of asthma and inflammation (see J. L. Marx, *Science,* 1982, 215, 1380–1383) as well as of endotoxic shock (see J. A. Cook, et al., *J. Pharma col. Exp. Ther.,* 1985, 235, 470) and traumatic shock (see C. Denzlinger, et al., *Science* 1985, 230, 330). Thus, the compounds of formula I may be useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.,* 1979, 211, 436) and as also described in European Patent Application publication number 0 179 619 A1.

The selectivity of action of these compounds as leukotriene antagonists as opposed to non-specific smooth muscle depressants may be shown by carrying out the above in vitro procedure using the non-specific spasmogen barium chloride at a concentration of $1.5 \times 10^{-3}$M, again in the presence of indomethacin at $8 \times 10^{-6}$M.

Alternatively, the antagonistic properties of a compound of formula I can be demonstrated in vitro by a receptor-ligand binding assay described by Aharony (*Fed. Proc.* 46: 691, (1987)). According to this procedure, membrane fractions, containing the LTD$_4$/E$_4$ receptors, are prepared from guinea-pig lung parenchyma and incubated for 30 minutes at 22° C. with 1 nM $^3$H-LTD$_4$ in the absence or presence of tested antagonist. Specific binding, determined under conditions that prevent enzymatic metabolism of $^3$H-LTD$_4$, is the net result of total $^3$H-LTD$_4$ binding minus nonspecific binding determined in the presence of 1–2000 fold excess unlabelled LTD$_4$. Each assay is done in duplicate and results (Ki values) are typically a mean of several such determinations in individual receptor batches.

The % inhibition by a tested antagonist, relative to control binding (vehicle alone), is expressed as a fraction of log[antagonist] concentration (in molar units) and the half-maximal inhibition (IC$_{50}$) determined by computerized non-linear least-square analysis. The binding constant (Ki) is then calculated from IC$_{50}$ by the Cheng-Prusoff equation:

$$Ki = \frac{IC_{50}}{\left[1 + \frac{[L]}{Kd}\right]}$$

where [L] is $^3$H-LTD$_4$ concentration and Kd is the affinity constant of LTD$_4$ to this receptor, determined separately for each batch. (*Biochem. Pharmacol.* 22: 3099–3108, 1973).

In general, the compounds of formula I tested demonstrated statistically significant activity as LTC$_4$, LTD$_4$ and/or LTE$_4$ antagonists in one of the above tests at a concentration of about $10^{-7}$M or much less. For example, in the above described test, a Ki value of $10^{-9}$M was determined for the compound of Example 4.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene LTD$_4$ (starting with 2 ml of a 30 microgram/ml solution) and the effect of the test compound on the average time of leukotriene initiated change in breathing pattern (such as onset of dyspnoea) recorded and compared with that in undosed, control guinea-pigs. In general, compounds of formula I tested produced a significant increase in the time of onset of leukotriene initiated breathing changes following either oral or intravenous administration or by inhalation at a dose of about 100 mg/kg, or much less, without any indication of untoward side-effects at several multiples of the minimum effective dose.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) evaporation of solvent was carried out using a rotary evaporator under reduced pressure (600–4000 pascals; 4.5–30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, DE, USA;

(iv) in general, the course of reactions was followed by TLC and reaction times are given for illustration only;

(v) melting points are uncorrected and (d) indicates decomposition: the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz, 250 MHz, 300 MHz or 400 MHz using $CDCl_3$, $DMSO-d_6$ or $CD_3OD$ as solvent; conventional abbreviations for signal shape are used, for example: s, singlet; d, doublet; m, multiplet; br, broad; etc.; in addition "Ar" signifies an aromatic group or signal;

(ix) reduced pressures are given as absolute pressures in pascals (Pa); other pressures are given as gauge pressures in bars:

(x) chemical symbols have their usual meanings: the following abbreviations have also been used: v (volume), w (weight); mp (melting point), l [liter(s)], ml (milliliters), g [gram(s)], mg [milligram(s)], min (minutes), h (hour); and (xi) solvent ratios are given in volume: volume (v/v) terms.

EXAMPLE 1

4-[5-[4-(Dimethylamino)-3-oxa-4-oxobutyl]-1-propylindol-3-ylmethyl]-3-methoxy-N-(2-methylphenylsulfonyl)benzamide a. Methyl 4-(5-cyanoindol-3-ylmethyl)-3-methoxybenzoate A mixture of 5-cyanoindole (10 g) and freshly prepared silver carbonate on diatomaceous earth (40.66 g) was stirred and heated under reflux in toluene (100 ml) for 18 h, under an atmosphere of nitrogen. The mixture was cooled to room temperature, methyl 4-bromomethyl-3-methoxybenzoate (22.7 g) added, and stirring continued for 4 h. Ethyl acetate (200 ml) was added, the mixture filtered through diatomaceous earth, the filter pad washed with ethyl acetate and the filtrate evaporated. The dark oil obtained was purified by flash chromatography, eluting with 45:45:10 hexane:methylene chloride:ethyl acetate, to give a foam which was crystallized from toluene to give methyl 4-(5-cyanoindol-3-ylmethyl)-3-methoxybenzoate (11.8 g, 53%) as white crystals; mp 148°–149°; partial NMR (250 MHz, $DMSO-d_6$): 3.83(s, 3H, $OCH_3$), 3.91(s, 3H, $OCH_3$), 4.08(s, 2H, $ArCH_2Ar'$), 8.00(s, 1H, $H^4$-indole), 11.49(br s, 1H, $H^1$-indole).

b. Methyl 4-(5-formylindol-3-ylmethyl)-3-methoxybenzoate

A solution of sodium hypophosphite monohydrate (24.8 g) in water (40 ml) was added to a solution of methyl 4-(5-cyanoindol-3-ylmethyl)-3-methoxybenzoate (11.33 g) in acetic acid (40 ml) and pyridine (80 ml). Raney nickel (approximately 2.5 g) was added as an aqueous slurry, and the mixture was heated at 50°–55° for 3 h (CAUTION:evolution of hydrogen!). Ethyl acetate (200 ml) was added to the cooled solution, the mixture was filtered through diatomaceous earth, the filter pad washed with ethyl acetate, the combined filtrate washed with 1M hydrochloric acid (4×200 ml, until the aqueous washings were acidic), water (2×100 ml) and brine, and dried ($MgSO_4$). The solvent was evaporated to give an oil which was purified by flash chromatography, eluting with 3:6:1 hexane:methylene chloride:ethyl acetate, giving a foam which was crystallized from a mixture of ethyl acetate and hexane to give methyl 4-(5-formylindol-3-ylmethyl)-3-methoxybenzoate (9.85 g, 86%) as white crystals: mp 117°–120°; partial NMR (250 MHz, $DMSO-d_6$) 3.83(s, 3H, $OCH_3$); 3.94(s, 3H, $OCH_3$), 4.12(s, 2H, $ArCH_2Ar'$), 8.10(s, 1H, $H^4$-indole), 9.94(s, 1H, CHO), 11.45 (br s, 1H, $H^1$-indole).

c. Methyl 4-(5-formyl-1-propylindol-3-ylmethyl)-3-methoxybenzoate

Sodium hydride (2.96 g of a 60% w/w dispersion in mineral oil) was added to dry dimethylformamide (DMF, 100 ml), under a nitrogen atmosphere. The mixture was stirred and cooled in an ice-bath, and a solution of methyl 4-(5-formylindol-3-ylmethyl)-3-methoxybenzoate (20 g) in DMF (75 ml) added slowly. After 1 h, 1-bromopropane (9.13 g) was added slowly. After 2 h, the mixture was carefully acidified with 2M hydrochloric acid (100 ml), extracted with ethyl acetate (twice), and the extract washed with 1M hydrochloric acid, water, and brine. The dried ($MgSO_4$) solution was evaporated, and the residue dissolved in ethyl acetate and filtered through a pad of silica gel. The filtrate was evaporated and the product crystallised from ether to give methyl 4-(5-formyl-1-propylindol-3-ylmethyl)-3-methoxybenzoate (19.2 g, 85%) as white needles; mp 98°–99°; partial NMR (250 MHz, $DMSO-d_6$): 0.82 (t, 3H, $CH_3$), 1.75 (m, 2H, $CH_2$), 3.83 (s, 3H, $OCH_3$), 3.92 (s, 3H, $OCH_3$), 4.1 (m, 4H, $ArCH_2Ar'$ and $NCH_2$), 9.95 (s, 1H, CHO).

d. Methyl 4-[5-(2-methoxyvinyl)-1-propylindol-3-ylmethyl]-3-methoxybenzoate

A solution of potassium tert-butoxide (0.92 g) in dry tetrahydrofuran (10 ml) was added to a stirred suspension of (methoxymethyl)triphenylphosphonium chloride (2.8 g) in tetrahydrofuran (30 ml) under a nitrogen atmosphere, at ice-bath temperature. After 15 min, a solution of methyl 4-(5-formyl-1-propylindol-3-ylmethyl)-3-methoxybenzoate (2.0 g) in tetrahydrofuran (20 ml) was added dropwise. After 30 min, the mixture was poured onto water, and acidified with 1M hydrochloric acid. The mixture was extracted with ethyl acetate (twice), and the extract washed with water, and brine, then dried ($MgSO_4$) and evaporated. The residue was dissolved in methylene chloride, ether was added to give a precipitate, and the isolated precipitate was purified by flash chromatography, eluting with 85:15 hexane:ethyl acetate, to give methyl 4-[5-(2-methoxyvinyl)-1-propylindol-3-ylmethyl]-3-methoxybenzoate (1.2 g, 56%) as an oil; partial NMR (300 MHz, DMSO-$d_6$): 0.80(t, 3H, $CH_3$), 1.70(m, 2H, $CH_2$), 3.60 and 3.70(2xs, 3H, $OCH_3$, E and Z isomers), 3.83(s, 3H, $OCH_3$), 3.90(s, 3H, $OCH_3$), 4.03(m, 4H, $NCH_2$, $ArCH_2Ar'$).

e. Methyl 4-[5-(2,2-dimethoxyethyl)-1-propylindol-3-ylmethyl]-3-methoxybenzoate para-Toluenesulfonic acid hydrate (0.55 g) was added to a stirred solution of methyl 4-[5-(2-methoxyvinyl)-1-propylindol-3-ylmethyl]-3-methoxybenzoate (0.2 g) in 1:1 methanol:methylene chloride (5 ml), under a nitrogen atmosphere. After 4 h, the mixture was evaporated at ambient temperature, and the product was purified by flash chromatography, eluting with 4:1 hexane:ethyl acetate, to give methyl 4-[5-(2,2-dimethoxyethyl)-1-propylindol-3-ylmethyl]-3-methoxybenzoate (0.19 g, 88%) as an oil; partial NMR (300 MHz, DMSO-$d_6$): 0.81(t, 3H, $CH_3$), 1.71(m, 2H, $CH_2$), 2.84(m, 2H, $CH_2$), 3.20(s, 6H, $2xOCH_3$), 3.83(s, 3H, $OCH_3$), 3.91(s, 3H, $OCH_3$), 4.02(m, 4H, $NCH_2$, $ArCH_2Ar'$), 4.50(t, 1H, CH).

f. Methyl 4-(5-formylmethyl-1-propylindol-3-ylmethyl)-3-methoxybenzoate

A solution of methyl 4-[5-(2,2-dimethoxyethyl)-1-propylindol-3-ylmethyl]-3-methoxybenzoate (0.46 g) in tetrahydrofuran (7 ml) and b 1M hydrochloric acid (3.6 ml) was stirred at ambient temperature for 11 h, under a nitrogen atmosphere. The mixture was poured onto water, extracted with ethyl acetate (twice), and the extract washed with water (twice), brine, and then dried ($MgSO_4$). The solvent was evaporated to give a dark oil which was used in the next step without further purification.

g. Methyl 4-[5-(2-hydroxyethyl)-1-propylindol-3-ylmethyl-3-methoxybenzoate

Sodium borohydride (0.027 g) was added to a stirred solution of methyl 4-[5-(formylmethyl)-1-propylindol-3-ylmethyl]-3-methoxybenzoate (0.54 g) in methanol (15 ml) under a nitrogen atmosphere. After 30 min, the solvent was evaporated. The residue was dissolved in ethyl acetate, washed with water (twice), brine, and then dried ($MgSO_4$) and evaporated. The product was purified by flash chromatography, eluting with 7:3 hexane:ethyl acetate, to give methyl 4-[5-(2-hydroxyethyl)-1-propylindol-3-ylmethyl]-3-methoxybenzoate (0.35 g, 65%) as an oil: partial NMR (300 MHz, DMSO-$d_6$): 0.80(t, 3H, $CH_3$), 1.70(m, 2H, $CH_2$), 2.74(t, 2H, $CH_2$), 3.56(t, 2H, $CH_2$), 3.83(s, 3H, $OCH_3$), 3.91(s, 3H, $OCH_3$), 4.03(m, 4H, $NCH_2$, $ArCH_2Ar'$).

h. Methyl 4-[5-[4-(dimethylamino)-3-oxa-4-oxobutyl]-1-propylindol-3-ylmethyl]-3-methoxybenzoate A solution of methyl 4-[5-(2-hydroxyethyl)-1-propylindol-3-ylmethyl]-3-methoxybenzoate (0.2 g) and dimethylcarbamyl chloride (0.43 g) in dry pyridine (5 ml) was stirred and heated under reflux, under a nitrogen atmosphere. After 8 h, the cooled mixture was evaporated. The residue was dissolved in ethyl acetate, washed with 1M hydrochloric acid (twice), water, and brine, then dried ($MgSO_4$), and evaporated. The product was purified by flash chromatography, eluting with 7:3 hexane:ethyl acetate, to give methyl 4-[5-[4-(dimethylamino)-3-oxa-4-oxobutyl]-1-propylindol-3-ylmethyl]-3-methoxybenzoate (0.19 g, 80%) as an oil; partial NMR (300 MHz, DMSO-$d_6$): 0.81 (t, 3H, $CH_3$), 1.71(m, 2H, $CH_2$), 2.75(br d, 6H, $2xNCH_3$), 2.88(t, 2H, $CH_2$), 3.83(s, 3H, $OCH_3$), 3.91(s, 3H, $OCH_3$), 4.04(m, 4H, NCH, $ArCH_2Ar'$), 4.12(t, 2H, $OCH_2$).

i. 4-[5-[4-(Dimethylamino)-3-oxa-4-oxobutyl]-1-propylindol-3-ylmethyl]-3-methoxybenzoic acid A solution of lithium hydroxide monohydrate (0.074 g) in water (1 ml) was added to a stirred solution of methyl 4-[5-[4-(dimethylamino)-3-oxa-4-oxobutyl]-1-propylindol-3-ylmethyl]-3-methoxybenzoate (0.16 g) in methanol (3 ml), under a nitrogen atmosphere. After 24 hr, the mixture was poured onto 1M hydrochloric acid and extracted with ethyl acetate (twice). The extract was washed (water, brine), dried ($MgSO_4$) and evaporated to give 4-[5-[4-(dimethylamino)-3-oxa-4-oxobutyl]-1-propylindol-3-ylmethyl]-3-methoxybenzoic acid (0.15 g, 97%) as an oil; partial NMR (300 MHz, DMSO-$d_6$): 0.81(t, 3H, $CH_3$), 1.71(m, 2H, $CH_2$), 2.75(br d, 6H, $2xNCH_3$), 2.89(t, 2H, $CH_2$), 3.90(s, 3H, $OCH_3$), 4.05(m, 4H, $NCH_2$, $ArCH_2Ar'$), 4.12(t, 2H, $OCH_2$).

j. 4-[5-[4-(Dimethylamino)-3-oxa-4-oxobutyl]-1-propylindol-3-ylmethyl]-3-methoxy-N-(2-methylphenylsulfonyl)benzamide A mixture of 4-[5-[4-(dimethylamino)-3-oxa-4-oxobutyl]-1-propylindol-3-ylmethyl]-3-methoxybenzoic acid (0.14 g), 4-dimethylaminopyridine (0.047 g), 1-(3-dimethylaminopropyl)-3-ethylcarbodiimide hydrochloride (0.074 g), and 2-methylbenzenesulfonamide (0.060 g) was dissolved in methylene chloride (3 ml), and the mixture was stirred under a nitrogen atmosphere for 18 h. The mixture was poured into 1M hydrochloric acid, extracted with ethyl acetate (twice), and the extract was washed with 1M hydrochloric acid, water, and brine. The dried ($MgSO_4$) solution was evaporated, and the residue precipitated from a mixture of methanol and 1M hydrochloric acid, to give the title compound (0.178 g, 94%), as an off-white powder: mp 93°–97°.

Analysis for $C_{32}H_{37}N_3O_6S$: Calculated: C, 64.95; H, 6.30; N, 7.10. Found: C, 65.00; H, 6.40; N, 6.91.

The starting methyl 4-bromomethyl-3-methoxy benzoate of part a, above, was prepared as follows:

k. Methyl 3-methoxy-4-methylbenzoate

A solution of 3-methoxy-4-methylbenzoic acid (6.0 g) in methanol (120 ml) was treated with acetyl chloride (6 ml) and stirred for 36 hours. The solution was evaporated. The residue was dissolved in methanol (100 ml) and the solution evaporated. This procedure was repeated to give methyl 3-methoxy-4-methylbenzoate (6.34 g, 98%) as a colorless oil; NMR (80 MHz, $CDCl_3$): 2.2(s, 3H, $CH_3$), 3.9(2s, 6H, 2 x $OCH_3$), 7.1(d, 1H), 7.5(m, 2H).

l. Methyl 4-bromomethyl-3-methoxybenzoate

A stirred solution of methyl 3-methoxy-4-methylbenzoate (121.2 g) in carbon tetrachloride (1.4 liter) was heated under gentle reflux with a 350 watt tungsten lamp and subjected to an air purge by means of a T-tube attached to a water aspirator. A solution of bromine (107.2 g) in carbon tetrachloride (500 ml) was added dropwise over 4 h. Evaporation of the solvent gave a light yellow solid which was triturated with 500 ml of 1:9 ether:hexane. The solid was collected by filtration to give methyl 4-bromomethyl-3-methoxybenzoate (111.7 g, 64%) as a pale yellow solid: mp 87°–90°; NMR (80 MHz, $CDCl_3$): 3.9(2s, 6H, 2 x $OCH_3$), 4.5(s, 2H, $BrCH_2$), 7.4(m, 3H).

EXAMPLE 2

4-[5-[2-(N',N'-Dimethylureido)ethyl]-1-propylindol-3-ylmethyl]-3-methoxy-N-(2-methylphenylsulfonyl)benzamide a. Methyl 4-[5-[2-(N',N'-dimethylureido)ethyl]-1-propylindol-3-ylmethyl]-3-methoxybenzoate.

Triethylamine (0.049 g) and diphenylphosphoryl azide (0.134 g) were added to a stirred suspension of methyl 4-[5-[2-(carboxy)ethyl]-1-propylindol-3-ylmethyl]-3-methoxybenzoate (0.2 g) in toluene (2 ml), under nitrogen, and the mixture heated under reflux for two hours. An excess of dimethylamine was bubbled through the cooled mixture, the resulting solution stirred at ambient temperature for 1 h, and then poured into 1 molar hydrochloric acid and ethyl acetate. The aqueous phase was extracted with ethyl acetate; and the combined organic phase washed (water, brine), dried ($MgSO_4$) and evaporated to give a viscous oil. The product was purified by flash chromatography, eluting with 4:6 ethyl acetate:methylene chloride, to give methyl 4-[5-[2-(N',N'-dimethylureido)ethyl]-1-propylindol-3-ylmethyl]-3-methoxybenzoate (0.2 g, 90%) as an oil; partial NMR (300 MHz, DMSO-$d_6$): 0.81 (t, 3H, $CH_3$), 1.70 (m, 2H, $CH_2$), 2.71 (m, 8H), 3.18 (m, 2H), 3.82 (s, 3H, $OCH_3$), 3.91 (s, 3H, $OCH_3$), 4.04 (m, 4H), 6.29 (t, 1H, NH).

b. 4-[5-[2-(N',N'-Dimethylureido)ethyl]-1-propylindol-3-ylmethyl]-3-methoxybenzoic acid Using a similar procedure to that described in Example 1, part i, except starting from methyl 4-[5-[2-(N',N'-dimethylureido)ethyl]-1-propylindol-3-ylmethyl]-3-methoxybenzoate, 4-[5-[2-(N'N'-dimethylureido)ethyl]-1-propylindol-3-ylmethyl]-3-methoxybenzoic acid was obtained (87%) as a pink powder; mp 95°–103° C.

c. 4-[5-[2-(N',N'-Dimethylureido)ethyl]-1-propylindol-3-ylmethyl]-3-methoxy-N-(2-methylphenylsulfonyl)benzamide.

Using a similar procedure to that described in Example 1, part j, except starting from 4-[5-[2-(N',N'-dimethylureido)ethyl]-1-propylindol-3-ylmethyl]-3-methoxybenzoic acid, the title compound was obtained (85%) as a powder: mp 115°–121° C.

Analysis for $C_{32}H_{38}N_4O_5S$:

Calculated: C, 65.06; H, 6.48; N, 9.48. Found: C, 64.79; H, 6.40; N, 9.67.

The methyl 4-[5-[2-(carboxy)ethyl]-1-propylindol-3-ylmethyl]-3-methoxybenzoate used in part a, above, was obtained as follows:

d. Methyl E-4-[5-[2-(t-butoxycarbonyl)vinyl]-1-propylindol-3-ylmethyl]-3-methoxybenzoate Using a similar procedure to that described in Example 8, part e, except starting from methyl 4-(5-formyl-1-propylindol-3-ylmethyl)-3-methoxybenzoate, and using tert-butyl (triphenylphosphoranylidene)acetate, methyl E-4-[5-[2-(t-butoxycarbonyl)vinyl]-1-propylindol-3-ylmethyl]-3-methoxybenzoate was obtained (98%) as a viscous oil: partial NMR (250 MHz, DMSO-$d_6$): 0.81(t, 3H, $CH_2CH_3$), 1.48(s, 9H, $C(CH_3)_3$), 1.75(m, 2H, $CH_2CH_3$), 3.82(s, 3H, $OCH_3$), 3.91(s, 3H, $OCH_3$), 6.38(d, J=15.8 Hz, 1H, CH=CH), 7.6(d, J=15.8 Hz, 1H, CH=CH).

e. Methyl 4-[5-[2-(t-butoxycarbonyl)ethyl]-1-propylindol-3-ylmethyl]-3-methoxybenzoate Using a similar procedure to that described in Example 8, part g, except starting from methyl E-4-[5-[2-(t-butoxycarbonyl)vinyl]-1-propylindol-3-ylmethyl]-3-methoxybenzoate, methyl 4-[5-[2-(t-butoxycarbonyl)ethyl]-1-propylindol-3-ylmethyl]-3-methoxybenzoate was obtained (100%) as a colorless oil; partial NMR (250 MHz, DMSO-$d_6$): 0.81(t, 3H, $CH_2CH_3$), 1.32(s, 9H, $C(CH_3)_3$), 2.50(t, 2H, $CH_2CH_2Ar$), 2.83(t, 2H, $CH_2CH_2Ar$), 3.83(s, 3H, $OCH_3$), 3.91(s, 3H, $OCH_3$).

f. Methyl 4-[5-[2-(carboxy)ethyl]-1-propylindol-3-ylmethyl]-3-methoxybenzoate Using a similar procedure to that described in Example 8, part f, except starting from methyl 4-[5-[2-(t-butoxycarbonyl)ethyl]-1-propylindol-3-ylmethyl]-3-methoxybenzoate, methyl 4-[5-[2-(carboxy)ethyl]-1-propylindol-3-ylmethyl]-3-methoxybenzoate was obtained (80%) as white needles; mp 109°–111° C.; partial NMR (250 MHz, DMSO-$d_6$): 0.80(t, 3H, $CH_2CH_3$), 1.70(m, 2H, $CH_2CH_2CH_3$), 2.50(t, 2H, $CH_2CH_2Ar$), 2.85(t, 2H, $CH_2CH_2Ar$), 3.83(s, 3H, $OCH_3$), 3.91(s, 3H, $OCH_3$).

EXAMPLE 3

4-[5-[2-[(Morpholinocarbonyl)amino]ethyl]-1-propylindol-3-ylmethyl]-3-methoxy-N-(2-methylphenylsulfonyl)benzamide a. Methyl 4-[5-[2-[(morpholinocarbonyl)amino]ethyl]-1-propylindol-3-ylmethyl]-3-methoxybenzoate Using a similar procedure to that described in Example 2, part a, except using morpholine instead of dimethylamine, methyl 4-[5-[2-[(morpholinocarbonyl)amino]ethyl]-1-propylindol-3-ylmethyl]-3-methoxybenzoate was obtained (93%) as a foam; partial NMR (300 MHz, DMSO-$d_6$): 0.81 (t, 3H, $CH_3$), 1.71 (m, 2H), 2.72 (m, 2H), 3.20 (m, 6H), 3.51 (m, 4H), 3.83 (s, 3H, $OCH_3$), 3.92 (s, 3H, $OCH_3$), 4.02 (m, 2H), 6.60 (t, 1H, NH).

b. 4-[5-[2-[(Morpholinocarbonyl)amino]ethyl]-1-propylindol-3-ylmethyl]-3-methoxybenzoic acid Using a similar procedure to that described in Example 2, part b, except starting from methyl 4-[5-[2-[(morpholinocarbonyl)amino]ethyl]-1-propylindol-3-ylmethyl]-3-methoxybenzoate, 4-[5-[2-[(morpholinocarbonyl)amino]ethyl]-1-propylindol-3-ylmethyl]-3-methoxybenzoic acid was obtained (84%) as a powder: mp 105°–113° C.

c. 4-[5-[2-[(Morpholinocarbonyl)amino]ethyl]-1-propylindol-3-ylmethyl]-3-methoxy-N-(2-methylphenylsulfonyl)benzamide Using a similar procedure to that described in Example 2, part c, except starting from 4-[5-[2-[(morpholinocarbonyl)amino]ethyl]-1-propylindol-3-ylmethyl]-3-methoxybenzoic acid, the title compound was as a powder; mp 117°–123° C.

Analysis for $C_{34}H_{40}N_4SO_6 \cdot 0.3 H_2O$: Calculated: C, 63.99; H, 6.41; N, 8.77. Found: C, 63.96; H, 6.37; N, 8.53.

EXAMPLE 4

4-[5-[2-N',N'-Dimethylureido)ethyl]-1-methylindol-3-ylmethyl]-3-methoxy-N-(2-methylphenylsulfonyl)benzamide a. Methyl 4-[5-[2-(N',N'-dimethylureido)ethyl]-1-methylindol-3-ylmethyl]-3-methoxybenzoate Using a similar procedure to that described in Example 2, part a, except starting from methyl 4-[5-[2-(carboxy)ethyl]-1-methylindol-3-ylmethyl]-3-methoxybenzoate, methyl 4-[5-[2-(N',N'-dimethylureido)ethyl]-1-methylindol-3-ylmethyl]-3-methoxybenzoate was obtained (77%) as a white solid; mp 122.5°–123.5° C.

b. 4-[5-[2-(N',N'-Dimethylureido)ethyl]-1-methylindol-3-ylmethyl]-3-methoxybenzoic acid Using a similar procedure to that described in Example 2, part b, except starting from methyl 4-[5-[2-(N',N'-dimethylureido)ethyl]-1-methylindol-3-ylmethyl]-3-methoxybenzoate, 4-[5-[2-(N',N'-dimethylureido)ethyl]-1-methylindol-3-ylmethyl]-3-methoxybenzoic acid was obtained (90%) as a white solid: mp 195°–196° C.

c. 4-[5-[2-(N',N'-Dimethylureido)ethyl]-1-methylindol-3-ylmethyl]-3-methoxy-N-(2-methylphenylsulfonyl)benzamide Using a similar procedure to that described in Example 2, part c, except starting from 4-[5-[2-(N',N'-dimethylureido)ethyl]-1-methylindol-3-methoxybenzoic acid, the title compound was obtained (91%) as a white solid: mp 124°–131° C.

Analysis for $C_{30}H_{34}N_4O_5S$: Calculated: C, 64.04; H, 6.09; N, 9.96. Found: C, 63.90; H, 6.15; N, 9.97.

The methyl 4-[5-[2-(carboxy)ethyl]-1-methylindol-3-ylmethyl]-3-methoxybenzoate (mp 162°–163° C.), used in part a, above, was obtained from methyl 4-(5-formyl-1-methylindol-3-ylmethyl)-3-methoxybenzoate (Example 8, part d) using similar procedures to those described in Example 2, parts d, e and f.

EXAMPLE 5

4-[5-[2-(N',N'-Dimethylureido)ethyl]-1-methylindol-3-ylmethyl]-3-methoxy-N-(2-chlorophenylsulfonyl)benzamide Using a similar procedure to that described in Example 2, part c, except starting from 4-[5-[2-(N',N'-dimethylureido)ethyl]-1-methylindol-3-methoxybenzoic acid, and using 2-chlorophenylsulfonamide instead of 2-methylphenylsulfonamide, the title compound was obtained (76%) as a white solid; mp 208°–211° C.

Analysis for $C_{29}H_{31}ClN_4O_5S$: Calculated: C, 59.74; H, 5.36; N, 9.61. Found: C, 59.56; H, 5.36; N, 9.62.

EXAMPLE 6

4-[5-[2-[(Morpholinocarbonyl)amino]ethyl]-1-methylindol-3-ylmethyl]-3-methoxy-N-(2-methylphenylsulfonyl)benzamide a. Methyl 4-[5-[2-[(morpholinocarbonyl)amino]ethyl]-1-methylindol-3-ylmethyl]-3-methoxybenzoate Using a similar procedure to that described in Example 2, part a, except starting from methyl 4-[5-[2-(carboxy)ethyl]-1-methylindol-3-ylmethyl]-3-methoxybenzoate, and using morpholine instead of dimethylamine, methyl 4-[5-[2-[(morpholinocarbonyl)amino]ethyl]-1-methylindol-3-ylmethyl]-3-methoxybenzoate was obtained (73%) as a white solid: mp 160°–161° C.

b. 4-[5-[2-[(Morpholinocarbonyl)amino]ethyl]-1-methylindol-3-ylmethyl]-3-methoxybenzoic acid Using a similar procedure to that described in Example 2, part b, except starting from methyl 4-[5-[2-[(morpholinocarbonyl)amino]ethyl]-1-methylindol-3-ylmethyl]-3-methoxybenzoate, 4-[5-[2-[(morpholinocarbonyl)amino]ethyl]-1-methylindol-3-ylmethyl]-3-methoxybenzoic acid was obtained (88%) as a solid: mp 221°–226° C.

c. 4-[5-[2-[(Morpholinocarbonyl)amino]ethyl]-1-methylindol-3-ylmethyl]-3-methoxy-N-(2-methylphenylsulfonyl)benzamide Using a similar procedure to that described in Example 2, part c, except starting from 4-[5-[2-[(morpholinocarbonyl)amino]ethyl]-1-methylindol-3-ylmethyl]-3-methoxybenzoic acid, the title compound was obtained (87%) as a white solid: mp 125°-133° C.

Analysis for $C_{32}H_{36}N_4O_6S$: Calculated: C, 63.56; H, 6.00; N, 9.26. Found: C, 63.68; H, 6.04; N, 9.29.

EXAMPLE 7

4-[5-[2-[(Morpholinocarbonyl)amino]ethyl]-1-methylindol-3-yl-methyl]-3-methoxy-N-(2-chlorophenylsulfonyl)benzamide Using a similar procedure to that described in Example 2, part c, except starting from 4-[5-[2-[(morpholinocarbonyl)amino]ethyl]-1-methylindol-3-ylmethyl]-3-methoxybenzoic acid, and using 2-chlorophenylsulfonamide instead of 2-methylphenylsulfonamide, the title compound was obtained (45%) as a white solid; mp 175°-181° C.

Analysis for $C_{31}H_{33}ClN_4O_6S \cdot 0.4\ H_2O$: Calculated: C, 58.88; H, 5.39; N, 8.86. Found: C, 59.02; H, 5.32; N, 8.84.

EXAMPLE 8

4-[5-[2-(N',N'-Dimethylureido)propyl]-1-methylindol-3-ylmethyl]-3-methoxy-N-(2-methylphenylsulfonyl)-benzamide a. Methyl 4-[5-[2-(N',N'-dimethylureido)propyl]-1-methylindol-3-ylmethyl]-3-methoxybenzoate Using a similar procedure to that described in Example 2, part a, except starting from methyl 4-[5-[2-(carboxy)propyl]-1-methylindol-3-ylmethyl]-3-methoxybenzoate, methyl 4-[5-[2-(N',N'-dimethylureido)-propyl]-1-methylindol-3-ylmethyl]-3-methoxybenzoate was obtained (71%) as a gum: partial NMR (300 MHz, DMSO-$d_6$). 0.98 (d, 3H, CH$_3$), 2.52-2.62 (m, 1H), 2.71 (s, 6H), 2.78-2.88 (m, 1H), 3.69 (s, 3H, CH$_3$), 3.73-3.85 (m, 4H), 3.92 (s, 3H, OCH$_3$), 4.00 (s, 3H, OCH$_3$), 5.88 (d, 1H, NH).

b. 4-[5-[2-(N',N'-Dimethylureido)propyl]-1-methylindol-3-ylmethyl]-3-methoxybenzoic acid Using a similar procedure to that described in Example 2, part b, except starting from methyl 4-[5-[2-(N',N'-dimethylureido)propyl]-1-methylindol-3-ylmethyl]-3-methoxybenzoate, 4-[5-[2-(N',N'-dimethylureido)-propyl]-1-methylindol-3-ylmethyl]-3-methoxybenzoic acid was obtained (95%) as a white solid: mp 162°-163° C.

c. 4-[5-[2-(N',N'-Dimethylureido)propyl]-1-methylindol-3-ylmethyl]-3-methoxy-N-(2-methylphenylsulfonyl)-benzamide Using a procedure similar to that described in Example 2, part c, except starting from 4-[5-[2-(N',N'-dimethylureido)propyl]-1-methylindol-3-ylmethyl]-3-methoxybenzoic acid, the title compound was obtained (70%) as a white solid: mp 125°-135° C.

Analysis for $C_{31}H_{36}N_4O_5S$: Calculated: C, 64.56; H, 6.29; N, 9.71. Found: C, 64.35; H, 6.11; N, 9.61.

The methyl 4-[5-[2-(carboxy)propyl]-1-methylindol-3-ylmethyl]-3-methoxybenzoate used in part a, above, was obtained as follows:

d. Methyl 4-(5-formyl-1-methylindol-3-ylmethyl)-3-methoxybenzoate

Sodium hydride (1.23 g of a 60% dispersion in mineral oil) was added to dry N,N-dimethylformamide (100 ml), under an atmosphere of nitrogen. The mixture was cooled in an ice-bath, a solution of methyl 4-(5-formylindol-3-ylmethyl)-3-methoxybenzoate (9.0 g) in N,N-dimethylformamide (20 ml) added slowly, and the mixture stirred for 1 hr. Methyl iodide (4.34 g) was added slowly, stirring continued for 2.5 hr., then the mixture carefully acidified with hydrochloric acid (100 ml) to give an off-white precipitate which was purified by flash chromatography, eluting with 45:50:5 hexane:methylene chloride:ethyl acetate, to give a yellow oil which was crystallized from a mixture of ethyl acetate and hexane to give methyl 4-(5-formyl-1-methylindol-3-ylmethyl)-3-methoxybenzoate (7.6 g, 81%) as an off-white powder: mp 116°-118° C.; partial NMR(250 MHz, DMSO-$d_6$): 3.80 (s, 3H, OCH$_3$), 3.83(s, 3H, NCH$_3$), 3.93(s, 3H, OCH$_3$), 4.11(s, 2H, ArCH$_2$Ar'), 8.12(s, 1H, H$^4$-indole), 9.96 (s, 1H, CHO).

e. Methyl E-4-[5-[2-(t-butoxycarbonyl)-1-propenyl]-1-methylindol-3-ylmethyl]-3-methoxybenzoate A mixture of t-butyl (triphenylphosphoranylidene)-propionate (10.41 g) and methyl 4-(5-formyl-1-methylindol-3-ylmethyl)-3-methoxybenzoate (4.5 g) in dry dioxane (60 ml) was stirred and heated at 100° for 18 hr, under an atmosphere of nitrogen. After ethyl acetate (100 ml) was added to the cooled reaction solution, solids were removed by filtration and the filtrate evaporated. The residual dark oil was purified by flash chromatography, eluting with 45:50:5 hexane: methylene chloride:ethyl acetate, to give methyl E-4-[5-[2-(t-butoxycarbonyl)-1-propenyl]-1-methylindol-3-ylmethyl]-3-methoxybenzoate (5.4 g, 90%) as a white foam; partial NMR (250 MHz, DMSO-$d_6$): 1.49 (s, 9H, t-butyl), 2.01(d, J=1.0 Hz, 3H, CCH$_3$), 3.74(s, 3H), 3.82(s, 3H), 3.90(s, 3H), 4.05(s, 2H, ArCH$_2$Ar').

The t-butyl (triphenylphosphoranylidene)propionate was prepared as follows: Triphenylphosphine (33 g), t-butyl 2-bromopropionate (22 g) and triethylamine (12.7 g) were dissolved in ethyl acetate (150 ml), and stirred and heated under reflux for 48 hr, under an atmosphere of nitrogen. Methylene chloride (300 ml) was added to the cooled solution: the mixture was thoroughly washed with sodium hydroxide solution (10% w/w, 300 ml), water (200 ml) and brine; and dried (MgSO$_4$). The solvent was evaporated and the residual oil triturated with hexane (2x200 ml) to give t-butyl (triphenylphosphoranylidene)propionate (33 g, 67%) as a yellow powder; mp 144°-151° C.; partial NMR (250 MHz, CDCl$_3$): 1.0(br signal, 9H, t-butyl), 1.55(d, J=14.4 Hz, 3H, CH$_3$), 7.3-7.9(complex m, 15H, ArH).

f. Methyl E-4-[5-(2-carboxy-1-propenyl)-1-methylindol-3-ylmethyl]-3-methoxybenzoate.

Trifluoroacetic acid (50 ml) was added to a solution of methyl E-4-[5-[2-(t-butoxycarbonyl)-1-propenyl]-1-methylindol-3-ylmethyl]-3-methoxybenzoate (6.4 g) in a small volume of methylene chloride (10 ml) cooled in an ice-bath. After 1.5 hr, the solution was evaporated (at approximately room temperature), and the residue was crystallized from methanol to give methyl E-4-[5-(2- carboxy-1-propenyl)-1-methylindol-3-ylmethyl]-3-methoxybenzoate (4.2 g, 75%) as a white powder: mp 182°–183° C.; partial NMR (250 MHz, DMSO-$d_6$): 2.03(s, 3H, CCH$_3$), 3.75(s, 3H), 3.83(s, 3H), 3.90 (s, 3H), 4.06(s, 2H, ArCH$_2$Ar').

g. Methyl 4-[5-(2-carboxypropyl)-1-methylindol-3-yl-methyl]-3-methoxybenzoate.

Palladium on carbon (10% w/w, 0.3 g) was added to a solution of methyl E-4-[5-(2-carboxy-1-propenyl)-1-methylindol-3-ylmethyl]-3-methoxybenzoate (4.14 g) in redistilled tetrahydrofuran (75 ml) in a hydrogenation bottle. The mixture was hydrogenated at 2.7 bar for 4 hr. The catalyst was removed by filtration through diatomaceous earth, the filter pad was washed with tetrahydrofuran, and the filtrate evaporated. The residue was crystallized from methanol to give methyl 4-[5-(2-carboxypropyl)-1-methylindol-3-crystals: mp 149°–151° C.; partial NMR (250 MHz, DMSO-$d_6$): 1.0(d, CHCH$_3$), 2.60(m, 2H, CHCH$_2$Ar), 3.34(m, 1H, CHCH$_2$), 3.67(s, 3H), 3.83(s, 3H), 3.91(s, 3H), 3.99(s, 2H, ArCH$_2$Ar'), 12.05(s, 1H, COOH).

EXAMPLE 9

4-[5-[2-(N',N'-Dimethylureido)propyl]-1-methylindol-3-ylmethyl]-3-methoxy-N-(2-chlorophenylsulfonyl)-benzamide.

Using a similar procedure to that described in Example 2, part c, except starting from 4-[5-[2-(N',N'-dimethylureido)propyl]-1-methylindol-3-ylmethyl]-3-methoxybenzoic acid, and using 2-chlorophenylsulfonamide instead of 2-methylphenylsulfonamide, the title compound was obtained (88%) as a white solid; mp 131°–136° C.

Analysis for C$_{30}$H$_{33}$ClN$_4$S.0.4 H$_2$O: Calculated: C, 59.62; H, 5.64; N, 9.27. Found: C, 59.56; H, 5.58; N, 9.57.

EXAMPLE 10

4-[2-Chloro-5-[2-(N',N'-dimethylureido)propyl]-1-methylindol-3-ylmethyl]-3-methoxy-N-(2-methylphenylsulfonyl)benzamide a. Methyl 4-[2-chloro-5-[2-(N',N'-dimethylureido)propyl]-1-methylindol-3-ylmethyl]-3-methoxybenzoate.

N-Chlorosuccinimide (0.437 g) was added in one portion to a stirred solution of methyl 4-[5-[2-(N',N'-dimethylureido)propyl]-1-methylindol-3-ylmethyl]-3-methoxybenzoate (1.3 g) in dry dichloromethane (25 ml), under a nitrogen atmosphere. After 10 minutes, the solvent was evaporated, and the product purified by flash chromatography, eluting with 3:7 ethyl acetate:toluene, to give, after crystallization from ethyl acetate, methyl 4-[2-chloro-5-[2-(N',N'-dimethylureido)propyl]-1-methylindol-3-ylmethyl]-3methoxybenzoate (45%) as a white solid; mp 148° C.; NMR (300 MHz, DMSO-$d_6$). 0.96 (d, 3H, CH$_3$), 2.50–2.60 (m, 1H), 2.68 (s, 6H), 2.75–2.85 (m, 1H), 3.68–3.86 (m, 7H), 3.93 (s, 3H, OCH$_3$), 4.02 (s, 2H), 5.87 (d, 1H, NH), 6.95–7.05 (m, 2H), 7.19 (s, 1H), 7.37 (d, 1H), 7.40–7.55 (m, 2H).

b. 4-[2-Chloro-5-[2-(N',N'-dimethylureido)propyl]1-methylindol-3-ylmethyl]-3-methoxybenzoic acid Using a similar procedure to that described in Example 2, part b, except starting from methyl 4-[2-chloro-5-[2-(N',N'-dimethylureido)propyl]-1-methylindol-3-ylmethyl]-3-methoxybenzoate, 4-[2-chloro-5-[2-(N',N'-dimethylureido)propyl]-1-methylindol-3-methoxybenzoic acid was obtained (95%) as a white solid: mp 171°–173° C.

c. 4-[2-Chloro-5-[2-(N',N'-dimethylureido)propyl]1-methylindol-3-ylmethyl]-3-methoxy-N-(2-methylphenylsulfonyl)benzamide Using a similar procedure to that described in Example 2, part c, except starting from 4-[2-chloro-5-[2-(N',N'-dimethylureido)propyl]-1-methylindol-3-ylmethyl]-3-methoxybenzoic acid, the title compound was obtained (43%) as a white solid; mp 120°–130° C.

EXAMPLE 11

4-[2-Chloro-5-[2-(N',N'-dimethylureido)propyl]-1-methylindol-3-ylmethyl]-3-methoxy-N-(2-chlorophenylsulfonyl)benzamide Using a similar procedure to that described in Example 2, part c, except starting from 4-[2-chloro-5-[2-(N',N'-dimethylureido)propyl]-1-methylindol-3-ylmethyl]-3-methoxybenzoic acid, and using 2-chlorophenylsulfonamide instead of 2-methylphenylsulfonamide, the title compound was obtained (47%) as a white solid; mp 126°–136° C.

Analysis for C$_{30}$H$_{32}$Cl$_2$N$_4$O$_5$S.0.6 H$_2$O: Calculated: C, 56.09; H, 5.21; N, 8.72. Found: C, 56.19; H, 5.07; N, 8.70.

EXAMPLE 12

4-[2,6-Dichloro-5-[2-(N',N'-dimethylureido)propyl]-1-methylindol-3-ylmethyl]-3-methoxy-N-(2-methylphenylsulfonyl)benzamide.

a. Methyl 4-[2,6-dichloro-5-[2-(N',N'-dimethylureido)propyl]-1-methylindol-3-ylmethyl]-3-methoxybenzoate.

N-Chlorosuccinimide (0.313 g) was added in one portion to a stirred solution of methyl 4-[5-[2-(N',N'-dimethylureido)propyl]-1-methylindol-3-ylmethyl]-3-methoxybenzoate (0.5 g) in dichloromethane (25 ml). After 30 minutes, the solvent was evaporated, and the product isolated by flash chromatography, eluting with 3:7 ethyl acetate:toluene, to give methyl 4-[2,6-dichloro-5-[2-(N',N'-dimethylureido)propyl]-1-methylindol-3-ylmethyl]-3-methoxybenzoate (60%) as a white solid; mp 175°–176° C.; NMR (300 MHz, DMSO-$d_6$): 1.00 (d, 3H, CH$_3$), 2.61 (s, 6H), 2.82 (d, 2H), 3.72 (s, 3H, CH$_3$), 3.83 (s, 3H, OCH$_3$), 3.85–3.96 (m, 4H), 4.00 (s, 2H), 5.91 (d, 1H, NH), 6.99 (d, 1H), 7.33 (s, 1H), 7.38–7.50 (m, 2H), 7.61 (s, 1H).

b. 4-[2,6-Dichloro-5-[2-(N',N'-dimethylureido)propyl]-1-methylindol-3-ylmethyl]-3-methoxybenzoic acid Using a similar procedure to that described in Example 2, part b, except starting from methyl 4-[2,6-dichloro-5-[2-(N',N'-dimethylureido)propyl]-1-methylindol-3-ylmethyl]-3-methoxybenzoate, 4-[2,6-dichloro-5-[2-(N',N'-dimethylureido)propyl]-1-methylindol-3-ylmethyl]-3-methoxybenzoic acid was obtained (60%) as a white solid; mp 125°–135° C.

c.
4-[2,6-Dichloro-5-[2-(N',N'-dimethylureido)propyl]-1-methylindol-3-ylmethyl]-3-methoxy-N-(2-methylphenylsulfonyl)benzamide Using a similar procedure to that described in Example 2, part c, except starting from 4-[2,6-dichloro-5-[2-(N',N'-dimethylureido)propyl]-1-methylindol-3-ylmethyl]-3-methoxybenzoic acid, the title compound was obtained (77%) as a white solid: mp 136°–146° C.

Analysis for $C_{31}H_{34}Cl_2N_4O_5S.0.5\ H_2O$: Calculated: C, 56.88; H, 5.39; N, 8.56. Found: C, 56.60; H, 5.26; N, 8.51.

EXAMPLE 13

4-[2-Chloro-5-[2-(N',N'-dimethylureido)ethyl]-1-methylindol-3-ylmethyl]-3-methoxy-N-(2-methylphenylsulfonyl)benzamide a. Methyl 4-[2-chloro-5-[2-(N',N'-dimethylureido)ethyl]-1-methylindol-3-ylmethyl]-3-methoxybenzoate Using a similar procedure to that described in Example 10, part a, except starting from methyl 4-[5-[2-(N',N'-dimethylureido)ethyl]-1-methylindol-3-ylmethyl]-3-methoxybenzoate, methyl 4-[2-chloro-5-[2-(N',N'-dimethylureido)ethyl]-1-methylindol-3-ylmethyl]-3-methoxybenzoate was obtained (80%) as an oil; NMR (300 MHz, DMSO-$d_6$). 2.65–2.75 (m, 8H), 3.12–3.23 (m, 2H), 3.72 (s, 3H), 3.82 (s, 3H, OCH$_3$), 3.93 (s, 3H, OCH$_3$), 4.02 (s, 2H), 6.23 (t, 1H, NH), 6.98–7.08 (m, 2H), 7.19 (s, 1H), 7.39 (d, 1H), 7.40–7.50 (m, 2H).

b.
4-[2-Chloro-5-[2-(N',N'-dimethylureido)ethyl]-1-methylindol-3-ylmethyl]-3-methoxybenzoic acid Using a similar procedure to that described in Example 2, part b, except starting from methyl 4-[2-chloro-5-[2-(N',N'-dimethylureido)ethyl]-1-methylindol-3-ylmethyl]-3-methoxybenzoate, 4-[2-chloro-5-[2-(N',N'-dimethylureido)ethyl]-1-methylindol-3-ylmethyl]-3-methoxybenzoic acid was obtained (90%) as a white solid; mp 215° C.

4-[2-Chloro-5-[2-(N',N'-dimethylureido)ethyl]-1-methylindol-3-ylmethyl]-3-methoxy-N-(2-methylphenylsulfonyl)benzamide Using a similar procedure to that described in Example 2, part c, except starting from 4-[2-chloro-5-[2-(N',N'-dimethylureido)ethyl]-1-methylindol-3-ylmethyl]-3-methoxybenzoic acid, the title compound was obtained (68%) as a white solid: mp 222°–224° C.

Analysis for $C_{30}H_{33}ClN_4O_5S.0.2\ H_2O$: Calculated: C, 59.98; H, 5.60; N, 9.33. Found: C, 59.77; H, 5.55; N, 9.54.

EXAMPLE 14

4-[2-Chloro-5-[2-(N',N'-dimethylureido)ethyl]-1-methylindol-3-ylmethyl]-3-methoxy-N-(2-chlorophenylsulfonyl)benzamide Using a similar procedure to that described in Example 2, part c, except starting from 4-[2-chloro-5-[2-(N',N'-dimethylureido)ethyl]-1-methylindol-3-ylmethyl]-3-methoxybenzoic acid, and using 2-chlorophenylsulfonamide instead of 2-methylphenylsulfonamide, the title compound was obtained (94%) as a white solid: mp 204°–206° C.

Analysis for $C_{29}H_{30}Cl_2N_4O_5S$: Calculated: C, 56.40; H, 4.90; N, 9.07. Found: C, 56.27; H, 4.95; N, 9.19.

EXAMPLE 15

4-[2,6-Dichloro-5-[2-(N',N'-dimethylureido)ethyl]-1-methylindol-3-ylmethyl]-3-methoxy-N-(2-methylphenylsulfonyl)benzamide a. Methyl 4-[2,6-dichloro-5-[2-(N',N'-dimethylureido)ethyl]-1-methylindol-3-ylmethyl]-3-methoxybenzoate Using a similar procedure to that described in Example 12, part a, except starting from methyl [5-[2-(N',N'-dimethylureido)ethyl]-1-methylindol-3-ylmethyl]-3-methoxybenzoate, methyl 4-[2,6-dichloro-5-[2-(N',N'-dimethylureido)ethyl]-1-methylindol-3-ylmethyl]-3-methoxybenzoate was obtained (64%) as a white solid; mp 186°–189° C.; NMR (300 MHz, DMSO-$d_6$): 2.69 (s, 6H), 2.78–2.88 (m, 2H), 3.15–3.23 (m, 2H), 3.72 (s, 3H, CH$_3$), 3.83 (s, 3H, OCH$_3$), 3.93 (s, 3H, OCH$_3$), 4.01 (s, 2H), 6.30 (t, 1H, NH), 7.04 (d, 1H), 7.30 (s, 1H), 7.38–7.50 (m, 2H), 7.63 (s, 1H).

b.
4-[2,6-Dichloro-5-[2-(N',N'-dimethylureido)ethyl]-1-methylindol-3-ylmethyl]-3-methoxybenzoic acid Using a similar procedure to that described in Example 2, part b, except starting from methyl 4-[2,6-dichloro-5-[2-(N',N'-dimethylureido)ethyl]-1-methylindol-3-ylmethyl]-3-methoxybenzoate, 4-[2,6-dichloro-5-[2-(N',N'-dimethylureido)ethyl]-1-methylindol-3-ylmethyl]-3-methoxybenzoic acid was obtained (63%) as a white solid: mp 207° C.

c.
4-[2,6-Dichloro-5-[2-(N',N'-dimethylureido)ethyl]-1-methylindol-3-ylmethyl]-3-methoxy-N-(2-methylphenylsulfonyl)benzamide Using a similar procedure to that described in Example 2, part c, except starting from 4-[2,6-dichloro-5-[2-(N',N'-dimethylureido)ethyl]-1-methylindol-3-ylmethyl]-3-methoxybenzoic acid, the title compound was obtained (56%) as a white solid; mp 236°–238° C.

Analysis for $C_{30}H_{32}Cl_2N_4O_5S.1.20\ H_2O$: Calculated: C, 55.16; H, 5.30; N, 8,58. Found: C, 55.12; H, 4.99; N, 8.73.

EXAMPLE 16

The following illustrates representative pharmaceutical dosages forms which may be used for the therapeutic or prophylactic administration of a compound of formula I or of a pharmaceutically acceptable salt thereof (hereinafter referred to as 'Compound X'):

| (i) Tablet 1 | mg/tablet |
| --- | --- |
| 'Compound X' | 100.0 |
| Lactose | 182.75 |
| Croscarmellose Sodium | 12.0 |
| Starch | 2.25 |
| Magnesium stearate | 3.0 |
| (ii) Tablet 2 | mg/tablet |
| 'Compound X' | 20.0 |
| Microcrystalline cellulose | 420.0 |
| Polyvinylpyrrolidone | 14.0 |
| Starch | 43.0 |
| Magnesium stearate | 3.0 |
| (iii) Capsule | mg/capsule |
| 'Compound X' | 10.0 |
| Lactose | 488.5 |

-continued

| | | |
|---|---|---|
| | Magnesium stearate | 1.5 |
| (iv) | Injection 1 | (10 mg/ml) |
| | 'Compound X' (free acid form) | 1.0% w/v |
| | Sodium phosphate | 3.6% w/v |
| | 0.1 M Sodium hydroxide solution | 15.0% w/v |
| | Water for injection. . . . to 100% | |
| (v) | Injection 2 (buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 0.38% w/v |
| | Water for injection. . . . to 100% | |
| (vi) | Aerosol | mg/ml |
| | 'Compound X' | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.

Formulae

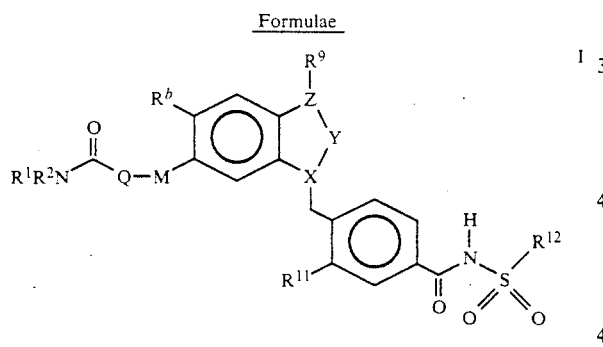

I

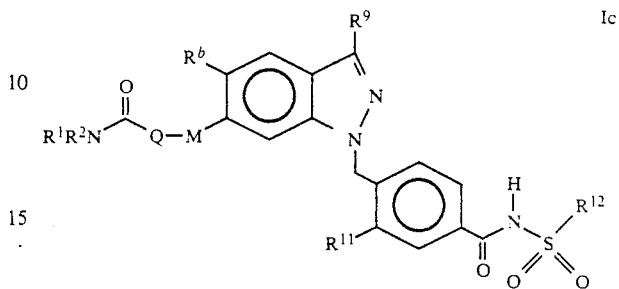

Ic

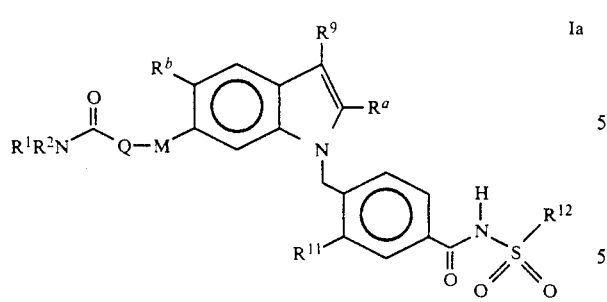

Ia

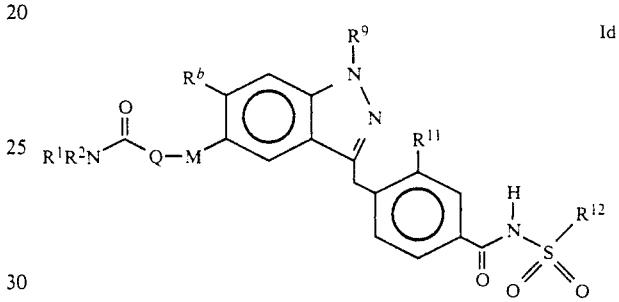

Id

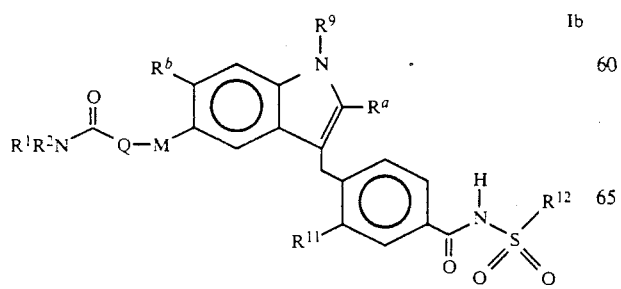

Ib

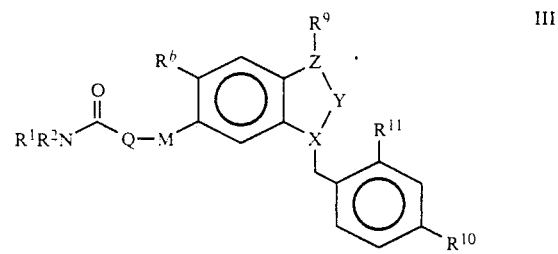

III

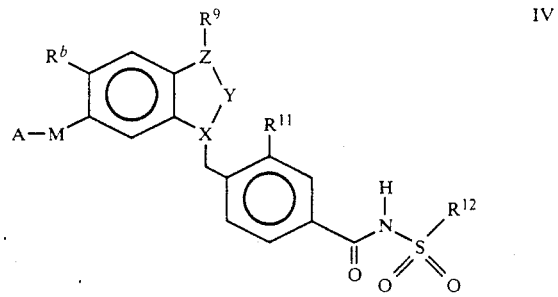

IV

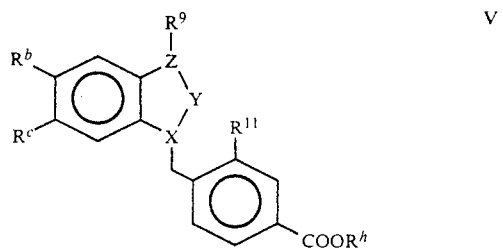

V 5,041,460
SCHEME Ia
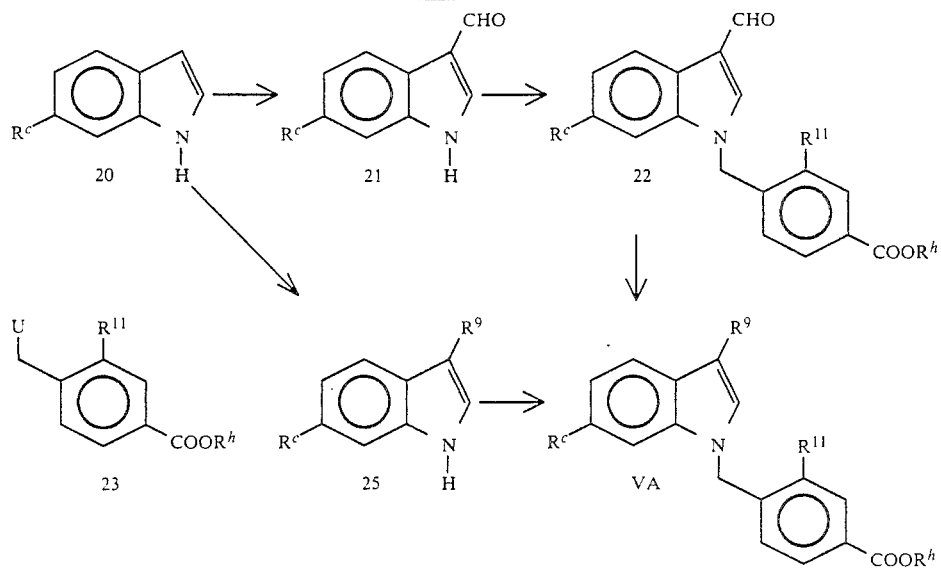
SCHEME Ib
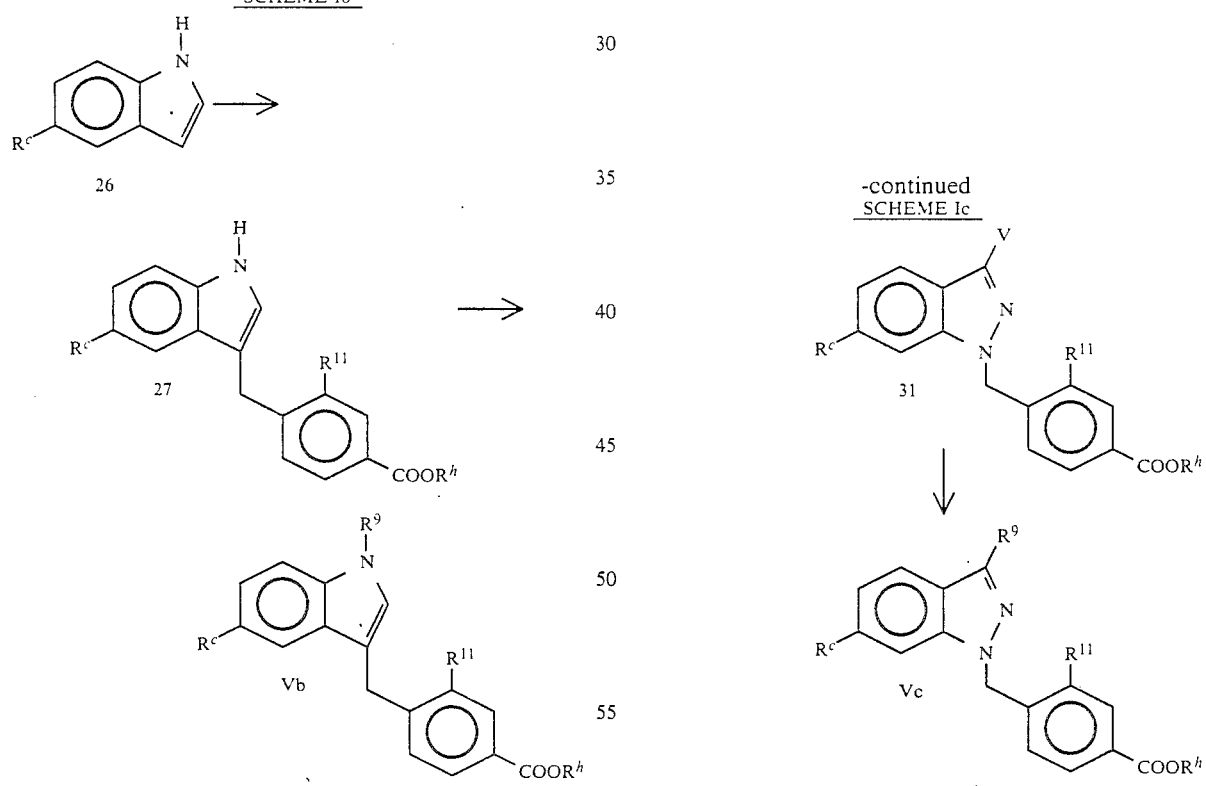
SCHEME Ic
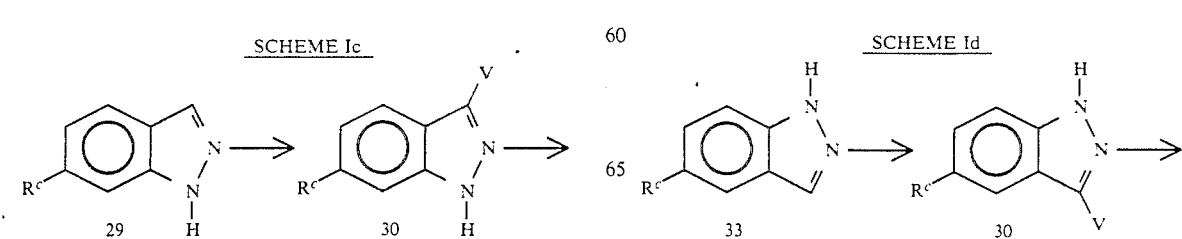

-continued
SCHEME Id
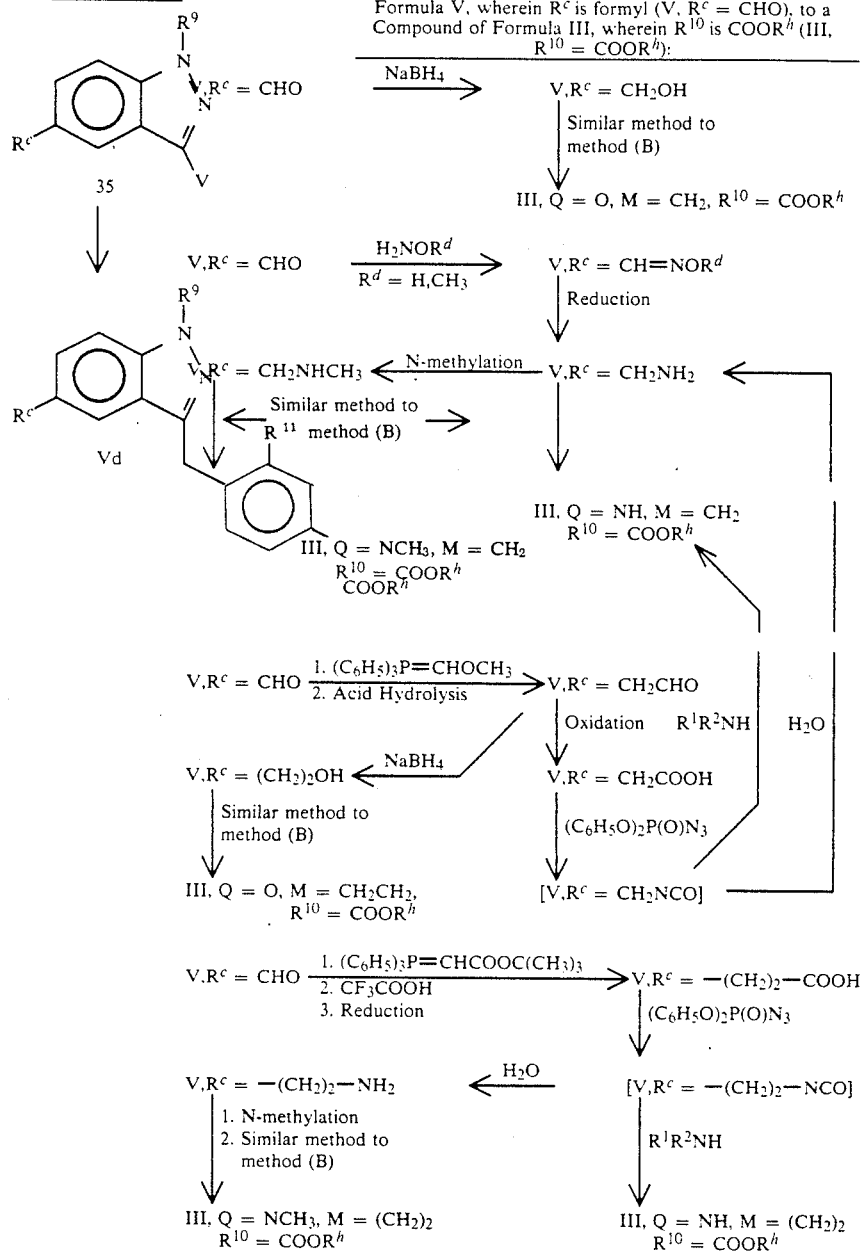
Scheme II: Examples of Routes from a Compound of Formula V, wherein $R^c$ is formyl (V, $R^c$ = CHO), to a Compound of Formula III, wherein $R^{10}$ is $COOR^h$ (III, $R^{10}$ = $COOR^h$):

-continued

Scheme II: Examples of Routes from a Compound of Formula V, wherein $R^c$ is formyl (V, $R^c$ = CHO), to a Compound of Formula III, wherein $R^{10}$ is COOR$^h$ (III, $R^{10}$ = COOR$^h$):

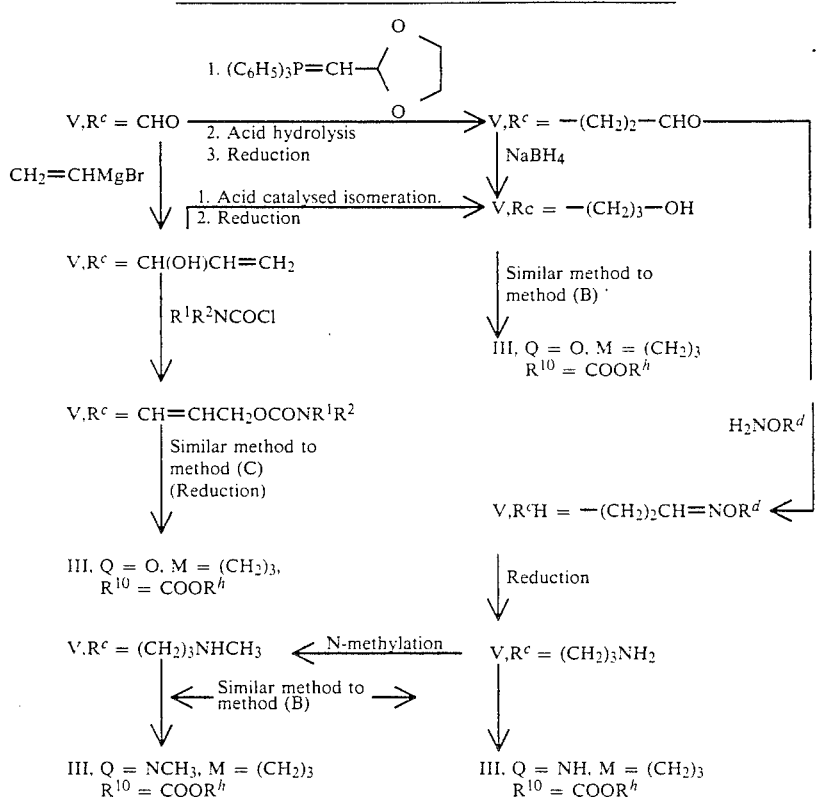

What is claimed is:

1. A compound of formula Ib', formula set out hereinbelow, the radicals $R^a$ and $R^b$ are together selected from a group consisting of
(i) $R^a$ and $R^b$ are each hydrogen,
(ii) $R^a$ is chloro and $R^b$ is hydrogen,
(iii) $R^a$ is bromo and $R^b$ is hydrogen and
(iv) $R^a$ and $R^b$ are each chloro;

the radicals $R^1$ and $R^2$ are selected from a group consisting of
(i) $R^1$ and $R^2$ are each independently selected from a group consisting of hydrogen, (1–6C)alkyl optionally containing a double or triple bond, (3–6C)cycloalkyl and (3–6C)cycloalkyl(1–4C)alkyl wherein a cycloalkyl group or the cycloalkyl portion of a cycloalkyl group may contain a double bond and may bear 1 or 2 (1–3C)alkyl groups, and
(ii) $R^1$ and $R^2$, together with the nitrogen to which they are attached, form a pyrrolidino, piperidino, piperazino, morpholino or thiomorpholino ring which ring may bear one to three methyl groups;

$R^9$ is selected from a group consisting of hydrogen, (1–6C)alkyl optionally containing a double or triple bond, (3–6C)cycloalkyl and (3–6C)cycloalkyl(1–4C)alkyl wherein a cycloalkyl group or the cycloalkyl portion of a cycloalkylalkyl group may contain a double bond and may bear 1 or 2 (1–3C)alkyl groups;

M is a (1–5C)alkylene group where Q is separated from the benzenoid ring by from 1 to 3 carbons;

$R^{11}$ is selected from a group consisting of hydrogen, (1–4C)alkoxy, (1–2C)alkyl and hydroxy; and $R^{12}$ is selected from a group consisting of (6–12C)aryl, theinyl, furyl, pyridyl and (6–12C)aryl(1–4-C)alkyl, in any of which the aromatic or heteroaromatic moiety may bear 1 or 2 substituents selected from a group consisting of halogen, (1–4C)alkyl, (1–4C)alkoxy, trifluoromethyl and amino;

or a pharmaceutically acceptable salt thereof.

2. A compound as claimed in claim 1 wherein $R^1$, $R^2$ or $R^9$ is, independently, methyl, ethyl propyl, isopropyl, butyl, 1-methylpropyl, 2-methylpropyl, pentyl, 1-ethylpropyl, 3-methylbutyl, hexyl, 4-methylpentyl, allyl, 2-methylprop-2-enyl, 3-methylbut-3-enyl, 2-propynyl, cyclopropyl, cyclobutyl, cyclopentyl, cyclohexyl, cyclopentyl, cyclohexenyl, methylcyclobutyl, cyclopropylmethyl, cyclobutylmethyl, cyclopentylmethyl, cyclohexylmethyl, 1-cyclopentylethyl, 2-cyclopentylethyl or methylcyclopentylethyl;

or $R^1$ and $R^2$, together with the nitrogen to which they are attached, form a pyrrolidino, piperidino, 4-methylpiperazino or morpholino ring;

M is methylene, ethan-1,2-diyl, propan-1,3-diyl, propan-1,2-diyl, 2-methylpropan-1,2-diyl or butan-1,3-diyl;

$R^{11}$ is methoxy, ethoxy, propoxy, methyl or ethyl; and $R^{12}$ is phenyl, naphthyl, thienyl, furyl, pyridyl, phenylmethyl, 2-phenylethyl or 3-phenylpropyl, wherein the aromatic or heteroaromatic portion may bear a fluoro, chloro, bromo, methyl, ethyl, methoxy, ethoxy, trifluoromethyl or amino substituent.

3. A compound as claimed in claim 1 wherein $R^1$, $R^2$ and $R^9$ are each independently selected from a group consisting of hydrogen, (1-4C)alkyl optionally containing a double bond; (3-5C)cycloalkyl and (3-5C)cycloalkyl(1-2C)alkyl; or $R^1$ and $R^2$, together with the nitrogen to which they are attached, form a pyrrolidino or morpholino ring;

M is a (1-3C)alkylene group;

$R^{11}$ is hydrogen or (1-2C)alkoxy; and $R^{12}$ is pyridyl, thienyl, or phenyl which may bear a methyl, chloro, bromo, fluoro or methoxy group.

4. A compound as claimed in claim 1 which is 4-[5-[4-(dimethylamino)-3-oxa-4-oxobutyl]-1-propylinodol-3-ylmethyl]-3-methoxy-N-(2-methylphenylsulfonyl)benzamide, or a pharmaceutically acceptable salt thereof.

5. A salt as claimed in claim 1, 2 or 3 wherein said salt is made with a base forming a physiologically acceptable cation.

6. A compound of the following formula

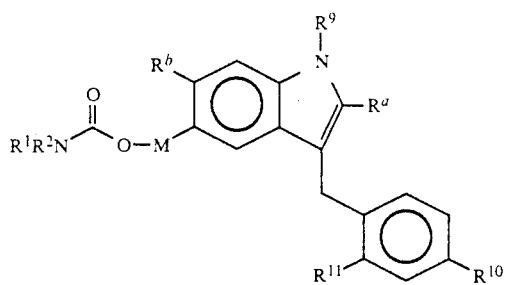

wherein $R^{10}$ is carboxy or a group of the formula $COOR^h$ where Rh is selected from a group consisting of phenyl, benzyl, and (1-6C)alkyl optionally bearing an acetoxy, (1-4C)alkoxy or (1-4C)alkylthio substituent, and M, $R^a$, $R^b$, $R^1$, $R^2$, $R^9$ and $R^{11}$ are defined as in claim 1, or a salt thereof.

7. A pharmaceutical composition comprising a leukotriene antagonizing amount of a compound of claim 1 or a pharmaceutically acceptable salt thereof and a pharmaceutically acceptable diluent or carrier.

8. A composition as claimed in claim 7 wherein said composition is in the form of a liquid or powdered aerosol.

9. A method of antagonizing the action of at least one type of leukotriene in a mammal requiring such treatment comprising administering to said mammal an effective amount of a compound of claim 1.

10. A method for the treatment of a selected allergic or inflammatory disorder in a mammal in need of such treatment comprising administering an effective amount of a compound of claim 1 to such mammal.

* * * * *